United States Patent [19]

Naskar et al.

[11] 4,089,879

[45] May 16, 1978

[54] SURFACE ACTIVE, LIQUID ESTER MIXTURES CONTAINING HYDROXYL, AND A METHOD OF PREPARING SAME

[75] Inventors: Sasanka Sekhar Naskar; Gustav Renckhoff, both of Witten; Wolfgang Heers, Wetter; Reinhard Pass, Witten, all of Germany

[73] Assignee: Dynamit Nobel Aktiengesellschaft, Cologne, Germany

[21] Appl. No.: 644,239

[22] Filed: Dec. 24, 1975

[30] Foreign Application Priority Data

| | | |
|---|---|---|
| Jan. 4, 1975 | Germany | 2500241 |
| Apr. 19, 1975 | Germany | 2517354 |
| Aug. 28, 1975 | Germany | 2538232 |

[51] Int. Cl.² .............................................. C11C 3/02
[52] U.S. Cl. ................................. 260/410.7; 260/410.6
[58] Field of Search .......................... 260/410.6, 410.7

[56] References Cited

U.S. PATENT DOCUMENTS

| | | | |
|---|---|---|---|
| 1,977,048 | 10/1934 | DeGroote et al. | 260/410.6 X |
| 1,977,089 | 10/1934 | Roberts | 260/410.6 X |
| 2,427,255 | 9/1947 | Burrell et al. | 260/410.6 X |
| 2,563,609 | 8/1951 | Matuszak | 260/410.6 X |
| 2,705,724 | 4/1955 | Cottle et al. | 260/410.6 X |
| 2,783,270 | 2/1957 | Polly et al. | 260/410.6 X |

*Primary Examiner*—Winston A. Douglas
*Assistant Examiner*—John F. Niebling
*Attorney, Agent, or Firm*—Burgess, Dinklage & Sprung

[57] ABSTRACT

Surface active, liquid, hydroxyl-containing mixed esters which are condensation products of:
(a) 1 mole of triethanolamine, glycerine, trimethylolpropane or pentaerythritol,
(b) 1 to 2 moles of a saturated, branched, aliphatic or cycloaliphatic carboxylic acid of 16 to 26 C atoms or mixtures thereof, and
(c) 0.1 to 0.9 moles, preferably 0.1 to 0.7 moles, of an aliphatic straight-chain or branched dicarboxylic acid of 3 to 10 C atoms, or mixtures thereof.

38 Claims, No Drawings

SURFACE ACTIVE, LIQUID ESTER MIXTURES CONTAINING HYDROXYL, AND A METHOD OF PREPARING SAME

The invention relates to surface active, liquid, hydroxyl-containing ester mixtures consisting of condensation products of (a) 1 mole of triethanolamine, glycerine, trimethylolpropane or pentaerythritol with (b) 1 to 2 moles of a saturated, branched, aliphatic or cycloaliphatic carboxylic acid having 16 to 26 carbon atoms, or mixtures of such acids, and (c) 0.1 to 0.9 moles, preferably 0.1 to 0.7 moles, of an aliphatic straight-chain or branched dicarboxylic acid of 3 to 10 carbon atoms, or mixtures of such acids. In general, the products have hydroxyl numbers of 20 to 260, saponification numbers of 150 to 350 and acid numbers of less than 5, preferably of less than 1. Component (a) can best be a monocarboxylic acid.

It is possible for one, more than one, or all of the substances, triethanolamine, glycerine, trimethylolpropane and pentaerythritol, to be present in the mixtures, as desired.

In the case of triethanolamine, dicarboxylic acids or their derivatives in amounts of up to 0.3 moles are preferred, and in amounts of up to 0.5 moles are greatly preferred, whereby products are formed having hydroxyl numbers from about 50 up, and saponification numbers up to about 250.

In the case of glycerine, dicarboxylic acids or their derivatives are preferred in amounts of 0.2 to 0.6 moles, which bring about the formation of products having the characteristics generally described above.

In the case of trimethylolpropane and pentaerythritol, the dicarboxylic acid component is preferred in amounts of 0.2 to 0.7 moles, whereby products of the general characteristics described are likewise formed.

The invention is especially directed to the object of obtaining surface-active substances, especially a liquid water-in-oil emulsifier, from technically available starting substances, by a simple, economical process. The products find application both in the cosmetic and in the pharmaceutical field, preferably in water-in-oil emulsions, and in the industrial field, for example in the sizing and preparation of fibers, or as a leather dubbing material.

The water-in-oil emulsifiers to be used for such purposes must be in liquid form with low solidification points for greater ease of handling, an HLB number of 3 to 7 being desirable for the achievement of stable water-in-oil emulsions. Aside from the viscous or semisolid or paste emulsifiers that are available on the market, there is only a small selection of liquid emulsifiers. Since these emulsifiers, however, frequently consist of unsaturated fatty esterification products, especially oleic acid esterification products, such as sorbitan oleates, pentaerythritoleates, polyglycerine ricinoleates, as well as wool wax and its derivatives, they have an unpleasant odor and a strong tendency to oxidize. These properties, especially in the cosmetics field, make it difficult to perfume water-in-oil emulsions obtained by the use of emulsifiers based on unsaturated fatty acids.

The object of the invention is the development and the economical manufacture of a surface active substance, especially a new water-in-oil emulsifier, having a good emulsion stability both at elevated temperature and below the freezing point, in fluid form insofar as possible for ease in handling, and in the form of a surface active product that is light in color and neutral in odor.

It has now been found that a fluid, emulsion-stabilizing surface active product of light color and neutral odor can be obtained, which does not have the disadvantages of the formerly available water-in-oil emulsifiers based on unsaturated fatty acid esterification products, such as unpleasant odor, dark color and viscous consistency, by esterifying 1 to 2 moles of a saturated, branched, aliphatic or cycloaliphatic monocarboxylic acid having 16 to 26 carbon atoms or a mixture of such acids, at 100° to 250° C, preferably in vacuo, to form hydroxyl-containing partial esters until an acid number under 50 and preferably under 1 is achieved, and simultaneously with their formation, or immediately thereafter, condensing the hydroxyl-containing partial esters with 0.1 to 0.9 moles of an aliphatic, straight-chain or branched dicarboxylic acid having 3 to 10 carbon atoms, or mixtures of such acids, or anhydrides thereof, preferably in vacuo, at temperatures of 100° to 220° C, until an acid number under 5, preferably under 1, is reached, and decolorizing and deodorizing the raw product in a conventional manner.

In the case of triethanolamine, temperatures up to 220° C and the above-specified amounts of the dicarboxylic acid component are preferred in the reaction with the monocarboxylic acids.

In the case of glycerine, temperatures of 160° C and up are preferred in the reaction with monocarboxylic acids and temperatures of 140° C and up are preferred in the reaction with the dicarboxylic acid component, with the use of the number of moles already mentioned.

In the case of trimethylolpropane and pentaerythritol, the lower temperature limits specified for glycerine are preferred, and preferably amounts of 0.2 to 0.7 moles of the dicarboxylic acid component.

As soon as the dicarboxylic acids or their anhydrides are added, the esterification is very preferably performed slowly, especially after cooling down to temperatures of 100° to 140° C, with a very slow raising of the temperature by 8° to 12° C per hour. A similar slow esterification is recommendable in the case of high proportions of triethanolamine in the range of 1 mole per 1.1 moles of monocarboxylic acid. In this manner the formation of resin by-products is reliably avoided.

The condensation products are mixtures in which a combining of the partial esters by the dicarboxylic acids takes place to a greater or lesser extent, depending on the molar ratios, it being possible both for the molecule of a dicarboxylic acid to become attached to two different molecules of the partial ester by the esterification of both of its carboxyl groups, and for one molecule of the partial ester to become attached to two different molecules of a dicarboxylic acid.

If the production is performed in vacuo, a vacuum as high as 350 Torr (pressure of 410 Torr) can be used in the preparation of the partial esters, and as high as 20 Torr in the condensation reaction with dicarboxylic acids.

In the preparation of the condensation products no esterification catalysts are required in general, but it is possible to use conventional esterification or transesterification catalysts, such as alkyl titanates, p-toluenesulfonic acids and quaternary ammonium salts, in amounts of 0.1 to 1%.

The required saturated, branched acids (b) are obtained by the catalytic treatment, with heating, of unsaturated fatty acids or oils containing such fatty acids, such as for example linseed oil, rape oil and fish oil. The dimeric and trimeric fatty acids which are also formed by such treatment are removed. The preparation of saturated, cyclic carboxylic acids (b) by the alkalization of linseed oil in aqueous media has been described extensively by R. E. Beal, R. A. Eisenhaur and V. E. Sohns, J. Am. Oil Chem-Soc., Vol. 42, 1115 (1965).

The dicarboxylic acids (c) used for the condensation of the partial esters can be straight-chained or branched. For example, malonic acid, succinic acid, fumaric acid, glutaric acid, adipic acid, sebacic acid, 2-ethylsuccinic acid, dimethylglutaric acid or trimethyl adipic acid and their anhydrides can be used. In the industrial field, partial esters condensed with maleic acid or maleic acid anhydride or branched dicarboxylic acids and their anhydrides can be used. The dicarboxylic acid can be saturated or unsaturated, e.g. mono-, di, etc. olefinically unsaturated.

The condensation products of triethanolamine partial esters with aliphatic dicarboxylic acids developed in accordance with the invention are characterized by special advantages:

1. They are light-colored, clear fluids of neutral odor, having a turbidity point of about $-5°$ C or, in the case of glycerine, from $0°$ to $20°$ C. They are soluble in petroleum jelly, paraffin oil, fatty alcohols, waxes, natural fats and oils, and they are distinguished by good distribution in the fatty phase in processing operations.

2. The precise establishment of a desired HLB number for water-in-oil emulsions is possible by means of adjusting the degree of condensation with varying proportions of aliphatic dicarboxylic acid. The HLB number itself is a measure of the ratio of hydrophilic to lipophilic groups in the emulsifier molecule. The HLB number of the emulsifiers of the invention can be established by preparing the partial esters with varying proportions of monocarboxylic acids of 16 to 26 carbon atoms, and condensing them in turn with varying proportions of dicarboxylic acids of 3 to 10 carbon atoms, while varying the HLB number so that it will be possible to associate with each fatty material a certain optimum HLB number that is required for this fatty phase. The HLB number will diminish as the proportion of the dicarboxylic acid increases. The HLB number will shift towards lower values as the proportion of mono- and dicarboxylic acids increases.

3. Stability against oxidation by the oxygen in the air when the emulsifier or the emulsions prepared therewith are in storage. The saturated, branched acids used in accordance with the invention in preparing the partial esters, and the condensation products carefully prepared therefrom are very stable against oxidation. Preference is given to the use of "isostearic acid," which is obtained by the catalytic treatment of linseed oil fatty acids (manufactured by Unilever-Emery N.V., Gouda, Holland), having a titer of $9°$ C, an iodine number of less than 7, a saponification number of 180 to 197, and an acid number from 175 to 191. This isostearic acid is a mixture of numerous isomeric, preferably methyl-branched $C_{18}$ fatty acids of low iodine numbers, which have good resistance to oxidation (H. Janistyn, *Handbuch der Kosmetika und Riechstoffe* (1969), Vol. 1, p. 533). Instead of isostearic acid, an easily obtainable mixture of iso acids of chain length 22, containing amounts of acids of other chain lengths, can be used, which can be obtained in the same manner as isostearic acid from rape oil containing erucic acid. Interaction with any active ingredients which may be incorporated in the cosmetic and pharmaceutical arts is impossible due to the saturated character of isostearic acid.

Triethanolamine and products made therefrom, such as salts, esters and addition products, are commercially obtainable in stabilized form. Likewise, glycerine, trimethylolpropane and pentaerythritol are easily obtainable commercially in pure form. Dicarboxylic acids--succinic acid anhydride, succinic acid, fumaric acid, malonic acid, glutaric acid, adipic acid, sebacic acid--are produced on a large technical scale, and their quality and purity are satisfactory. Succinic acid and fumaric acid are present in the human body where they occur as an intermediate in the citric acid cycle. Fumaric acid is an edible acid and is used in the U.S.A. as a substitute for fruit acid. Many of these dicarboxylic acids also occur in nature; for example, malonic acid, glutaric acid and adipic acid are found in the juice of the sugar beet. Consequently, the raw materials which are used in the products prepared in accordance with the invention are hygienically unobjectionable.

To prevent discoloration, nitrogen can be passed through the reaction mixture during the esterification, and also active charcoal can be added. After conventional deodorization, by means of steam and bleaching in vacuo with bleaching earth for example, a perfect, light-colored product of neutral odor is obtained, having no detectable peroxide content.

4. Shelf life of water-in-oil emulsions prepared with the condensation products developed in accordance with the invention.

The quality of an emulsifier, especially a water-in-oil emulsifier, can be determined on the basis of the stability of the emulsions prepared with it. The stability test is performed on water-in-oil emulsions as a rapid test, preferably at elevated temperatures, the quality of the emulsifier being characterized by the segregation of oil or water and/or by phase inversion to an oil-in-water emulsion (increase of conductivity).

The water-in-oil emulsions prepared with the condensation products of triethanolamine partial esters with aliphatic straight-chain and branched dicarboxylic acids developed in accordance with the invention for use as emulsifiers for the preparation of such emulsions showed no water segregation, hardly any oil segregation, and no appreciable change in conductivity relating to a phase inversion to an oil-in-water emulsion when stored at $25°$ C for 6 months, at $40°$ C for 3 months and at $55°$ C for two weeks. These good characteristics with regard to the stability of the water-in-oil emulsions were also evident in the freeze-thaw test that is part of the stability test and is performed in the $-15°$ to $+20°$ C temperature range.

From the consistencies of the emulsions prepared from the emulsifiers developed in accordance with the invention it can be concluded that, as the degree of condensation increases, i.e., as the molar proportion of the dicarboxylic acids increases, the viscosity of the emulsion decreases, and does so to such a degree that a cream-like consistency can be produced. This same phenomenon was observed as the number of $CH_2$ groups increased in the dicarboxylic acids used in the partial ester condensates.

The more highly condensed products having low hydroxyl numbers and high viscosity, in combination with the esters of high hydroxyl numbers, increase the stability of the very fluid water-in-oil emulsions prepared with them, and prevent oil separation.

Turbidity, which occurs, for example, at room temperature in the case of glycerine partial esters (cf. Examples 19 and 26), is observed in the condensation products of the invention only at decidedly lower temperatures, apparently due to the incorporation of the dicarboxylic acids. Increasing proportions of dicarboxylic acid lead step by step to a decided drop to lower turbidity points.

EXAMPLES

The following examples will serve to explain the invention further without, however, restricting it.

EXAMPLE 1

In a 10-liter three-necked flask equipped with stirrer, water separator, thermometer and gas feed tube, a mixture of 5112 g (18 moles) of isostearic acid (Type 5681 of Uniliver-Emery) and 2682 g (18 moles) of triethanolamine is heated for four hours at 200° C with stirring and the simultaneous passage of nitrogen through the reaction flask, and the water formed during the reaction is simultaneously removed. The characteristics of the ester thus produced can be seen in Table 1.

EXAMPLE 1a 1000 grams of the triethanolamine partial ester prepared in Example 1 is further esterified with 40 g of malonic acid in the 2-liter three-necked flask under a nitrogen atmosphere for four hours at 140° to 180° C (temperature rise 10° C/h), the flask being again equipped with the stirrer, thermometer, water separator and gas supply tube.

EXAMPLE 2

1000 g of triethanolamine partial ester, prepared as in Example 1, was esterified with 20 g of succinic acid anhydride in the manner described in Example 1a.

EXAMPLE 3

1000 g of triethanolamine partial ester was esterified with 40 g of succinic acid anhydride in the manner described in Example 1a.

Example 4

1000 g of triethanolamine partial ester was esterified with 60 g of succinic acid anhydride in the manner described in Example 1a.

EXAMPLE 5

1000 g of triethanolamine partial ester was esterified with 80 g of succinic acid anhydride as in Example 1a.

EXAMPLE 6

1000 g of triethanolamine partial ester was esterified with 50 g of fumaric acid in the manner described in Example 1a.

EXAMPLE 7

1000 g of triethanolamine partial ester was esterified with 60 g of adipic acid in the manner described in Example 1a.

EXAMPLE 8

1000 g of triethanolamine partial ester was esterified with 60 g of Sebacic acid in the manner described in Example 1 a.

EXAMPLE 9

In a 2-liter three-necked flask, a mixture of 1107 g (3.9 moles) of isostearic acid, 447 g (3.0 moles) of triethanolamine and 30 g (0.3 moles) of succinic acid anhydride was heated at 100° to 160° C for 6 hours (temperature rise 10° C/h) with intense stirring and under a nitrogen atmosphere, in the presence of 0.15 g of butyl titanate as catalyst plus 3 g of active charcoal. The water of reaction was removed at a vacuum of 20 Torr. Then the ester mixture thus obtained was deodorized for one hour at 160° C and bleached with 1% bleaching earth for one hour at 100° C, and then filtered in a pressure filter.

EXAMPLE 10

An ester mixture was prepared in the manner described in Example 9, but the amount of succinic acid anhydride used was 60 g instead of 30 g.

EXAMPLE 11

An ester mixture was prepared as described in Example 9, using 90 g of succinic acid.

EXAMPLE 12

A mixture of 1275 g (4.5 moles) of isostearic acid, 447 g (3.0 moles) of triethanolamine, 33 g (0.33 moles) of succinic acid anhydride and 2 g of active charcoal was heated with intense stirring under a nitrogen atmosphere for 6 hours from 100° C to 160° C (temperature rise 10° C/h) and the reaction water was removed at a vacuum of 20 Torr. The resultant ester mixture was deodorized for one hour at 160° C, bleached with 1% bleaching earth, and filtered in a pressure filter.

EXAMPLE 13

An ester mixture was prepared as in Example 12 with 66 g of succinic acid anhydride instead of 33 g.

EXAMPLE 14

An ester mixture was prepared with intense stirring under a nitrogen atmosphere from 1135 g (4 moles) of isostearic acid, 298 g (2.0 moles) of triethanolamine, 27 g (0.27 moles) of succinic acid anhydride, 0.15 g of butyl titanate and 3 g of activated charcoal in three hours at 140°–160° C and a vacuum of 20 Torr; then followed one hour of deodorizing at 160° C, a bleaching operation and a pressure filtration.

EXAMPLE 15

An ester mixture is prepared in six hours at 140° to 160° C (temperature rise 10° C/h) and a vacuum of 20 Torr from 620 g (2 moles) of a branched $C_{18}$ and $C_{22}$ iso acid which had been obtained by the thermal treatment of rape oil containing erucic acid in a manner analogous to the preparation of isostearic acid, 298 g (2 moles) of triethanolamine and 27 g (0.15 moles) of trimethyladipic acid, 0.1 g of butyl titanate and 2 g of active charcoal, and is then subjected to deodorization for one hour at 160° C, bleaching, and pressure filtration.

The properties and characteristics of the ester mixtures prepared in accordance with the examples are to be seen in the table that follows.

Table 1

Chemical and physical data on the examples listed under 1 to 15:

| Ex. | molar ratio TEA : IS | Amount of dicarboxylic acid in grams per 100 g of partial ester | Acid No. | Saponification No. | OH No. | HLB No. +0.5 | Density at 25° C | viscosity at 25° C in 25° C centipoises | Turbidity point in degrees C per DIN 51383 |
|---|---|---|---|---|---|---|---|---|---|
| 1 | 1 : 1.0 | — | 0.5 | 138 | 252 | 6.0 | 0.952 | 197.8 | −10 |
| 1a | 1 : 1.0 | 1 g malonic acid | 0.6 | 154 | 222 | 5.8 | 0.957 | 210.0 | −10 |
| 2 | 1 : 1.0 | 2 g succinic acid anhydride | 0.8 | 152 | 224 | 5.4 | 0.959 | 226.4 | − 8 |
| 3 | 1 : 1.0 | 4 g anhydride | 0.8 | 173 | 200 | 3.8 | 0.965 | 266.4 | − 7 |
| 4 | 1 : 1.0 | 6 g anhydride | 0.4 | 201 | 160 | 1.8 | 0.972 | 335.8 | − 6 |
| 5 | 1 : 1.0 | 8 g anhydride | 0.5 | 223 | 139 | 0.6 | 0.979 | 418.7 | − 6 |
| 6 | 1 : 1.0 | 5 g fumaric acid | 0.6 | 188 | 180 | 3.0 | 0.965 | 335.5 | − 6 |
| 7 | 1 : 1.0 | 6 g adinic acid | 0.6 | 178 | 196 | 3.2 | 0.967 | 266.5 | − 8 |
| 8 | 1 : 1.0 | 6 g sebacic acid | 0.9 | 170 | 200 | 3.3 | 0.960 | 276.4 | −10 |
| 9 | 1 : 1.3 | 2 g succinic acid anhydride | 0.4 | 174 | 150 | 3.0 | 0.951 | 195.7 | − 8 |
| 10 | 1 : 1.3 | 4 g anhydride | 0.6 | 193 | 130 | 2.0 | 0.957 | 239.5 | − 6 |
| 11 | 1 : 1.3 | 6 g anhydride | 0.7 | 212 | 122 | 0.6 | 0.965 | 298.7 | − 6 |
| 12 | 1 : 1.5 | 2 g succinic acid anhydride | 0.5 | 173 | 149 | 2.4 | 0.945 | 181.0 | − 8 |
| 13 | 1 : 1.5 | 4 g anhydride | 0.3 | 195 | 110 | 1.6 | 0.950 | 212.5 | − 5 |
| 14 | 1 : 2.0 | 2 g succinic acid anhydride | 0.9 | 180 | 62 | 2.0 | 0.934 | 151.5 | − 5 |
| 15 | 1 : 1.0 | 3 g trimethyladinic | 0.7 | 143 | 238 | 3.0 | 0.972 | 282.4 | − 6 |

IS = isostearic acid or iso-$C_{22}$ acid
TEA = triethanolamine

EXAMPLE 16

(Emulsion Tests)

The products of the condensation of triethanolaminisostearic acid partial esters with aliphatic straight-chain or branched dicarboxylic acids which are developed in accordance with the invention can be varied and fixed with regard to their degree of condensation or content of free hydroxyl groups, as the case may be, by appropriate management of the reaction and by changing the quantity ratios of the individual reactants, whereby any desired HLB number for water-in-oil emulsifiers can be achieved.

To show the outstanding properties of the surface active, fluid, hydroxyl-containing ester mixtures prepared in accordance with the invention, especially the highly desirable influence of the dicarboxylic acids, the ester mixtures described in the invention are compared as to their emulsifying action with two common commercial emulsifiers, e.g., pentaerythritol monooleate and sorbitan sesquioleate. Three different types of oil bases were selected. The emulsions were prepared by the following methods.

Fundamentally, the aqueous phase, heated at 70° C, was added with constant, intense stirring to the equally heated oily phase over a period of 5 minutes, and the mixture was cooled to 25° C over a period of 60 minutes. To compare the various emulsifiers, the emulsions thus prepared were subjected to stability tests at 25° C, 40° C and 55° C for 6 months, 4 months, and 2 weeks, respectively.

The storage of the prepared emulsions at various temperatures was divided up as follows:

1st Specimen — Storage at room temperature for 6 months in completely filled polystyrene containers.

2nd Specimen — Storage at 40° C for 3 months in 80% filled glass containers with screw lids.

3rd Specimen — Storage at 55° C for 2 weeks in 80% filled glass containers with screw lids.

4th Specimen — Thaw-freeze cycle: the specimen was kept for 16 h at −15° C and then for 8 h at +20° C.

In the appraisal of the decomposition phenomena observed in the storage tests (not in the thaw-freeze cycles), the following symbols are used:

O = unaltered
I = slight oil separation, max. 0.5 vol.-%
II = slight oil separation, approx. 0.5 - 1.0 vol.-%
III = greater oil separation, approx. 1.0 - 1.5 vol.-%
(+) = water-in-oil-stable water-in-oil emulsion
(−) = oil-in-water-stable water-in-oil emulsion or oil-in-water emulsion, as the case may be.

In the thaw-freeze cycles (G. A. Nowak, "Seifen - Oele - Fette - Wachse" 92, No. 3/1966), the number of cycles in which no decomposition phenomena were observed is listed in Tables 2 and 3.

In the thaw-freeze cycles water separation occurred in each case, while in the other stability tests it was oil separation that was observed.

Table 2

Type A Emulsion - Oil Base: Petroleum jelly (Pharmaline V-15 DAB 7) Composition of the emulsions:

Oil base 1: 27 wt.-parts petroleum jelly
3 wt.-parts emulsifiers of Examples 1 to 15

Water Phase: 0.3 wt.-parts $MgSO_4$
3.0 wt.-parts glycerine
0.2 wt.-parts p-hydroxybenzoic acid propyl ester
66.5 wt.-parts water

| Example No. | 6 Mos. 25° C | 3 Mos. 40° C | 2 wks. 55° C | Thaw-freeze cycles −13° C (16h), then 20° C (8h) |
|---|---|---|---|---|
| Pentaerythritol monooleate | O(+) | I(−) | II(−) | 4x |
| Sorbitan sesquioleate | O(+) | I(+) | II(+) | 8x |
| 1 | O(+) | I(+) | II(+) | 6x |
| 1a | O(+) | O(+) | O(+) | 12x |
| 2 | O(+) | O(+) | O(+) | 12x |
| 3 to 15 | all: O(+) | all: O(+) | O(30) a few I(+) | 10x a few 8x |

EXAMPLE 17

Preparation of a gel-like adsorption base and its use as a cream basis

In the case of the emulsifiers prepared in Examples 1 to 15, they have been compared in their emulsion stabilizing action in an adsorption base as a practical example.

COMPOSITION OF THE EMULSION 35 weight-parts of adsorption base (oil base 2)
65 weight-parts of aqueous phase
(62.5 wt.-parts water
0.3 wt.-parts MgSO$_4$
0.2 wt.-parts p-hydroxybenzoic acid propyl ester
2.0 wt.-parts sorbitol)

COMPOSITION AND PREPARATION OF THE ADSORPTION BASE

Oil base 2

40 wt.-parts paraffin oil
35 wt.-parts MIGLYOL 812 ® (Mfr. Dynamit Nobel)
7 wt.-parts BENTONE 27 ® (Titangesellschaft, Leverkusen) or BENTONE 34 ® in some cases
3 wt.-parts propylene glycol
25 wt.-parts of the emulsifiers of Examples 1 to 15.

The components of the adsorption base are vigorously stirred at 120° C for one hour. After this mixture has cooled down to 80° C, 35 wt.-parts of the gel-like adsorption base is diluted with 65 wt.-parts of aqueous phase having an 80° C temperature, with constant stirring.

Stirring is continued until the mass has cooled, and a smooth cream is obtained.

Table 3 shows the results of the stability tests.

Table 3

| Emulsion Type B - Oil basis: paraffin oil/triglyceride | | | | |
|---|---|---|---|---|
| Example No. | 6 Mos. 25° C | 3 Mos. 40° C | 2 wks. 55° C | Thaw-Freeze cycles −15° C (16h) then 20° C (8H) |
| Pentaerythritol monooleate | O(+) | I(−) | III(−) (−) | 4x |
| Sorbitan sesquioleate | O(+) | I(+) | II(+) | 8x |
| 1 | O(+) | O(+) | II(−) | 6x |
| 1a | O(+) | O(+) | O(+) | 10x |
| 2 | O(+) | O(+) | O(+) | 12x |
| 3 | O(+) | O(+) | O(+) | 12x |
| 4 to 15 | all O(+) | all O(+) | O(+) a few I(+) | 10x a few 8x |

EXAMPLE 18

The emulsifier prepared in Example 2 was tested for its emulsion stabilizing action in a water-in-oil lotion as a practical example.

Composition of the Emulsion 33 wt.-parts oil base 3
67 wt.-parts aqueous phase
(0.3 wt.-parts MgSO$_4$,
0.2 wt.-parts p-hydroxybenzoic acid propyl ester,
3.0 wt.-parts 70% sorbitol solution,
63.5 wt.-parts water)

COMPOSITION AND PREPARATION OF OIL BASE 3

45.0 wt.-parts paraffin oil
30.0 wt.-parts MIGLYOL ® 812 (Mfr., Dynamit Nobel)
20.0 wt.-parts of the emulsifier developed in Example 2
2.0 wt.-parts Bentone ® 27 (Titangesellschaft, Leverkusen)
3.0 wt.-parts propylene glycol The components of oil base 3 were stirred vigorously at 120° C for 1 hour. After the mixture had cooled to 80° C, 33 wt.-parts of this oil base were combined with 67 wt.-parts of aqueous phase whose temperature was also 80° C, and this mixture was cooled to 25° C with constant stirring over a period of at least one hour. The water-in-oil lotion thus obtained displayed no oil separation and no phase inversion after 2 weeks of storage at 40° C.

EXAMPLE 19

(Glycerine partial ester)

In a 10-liter three-necked flask equipped with stirrer, water separator, thermometer and gas feed tube, a mixture of 2024 g (22 moles) of glycerine and 6248 g (22 moles) of isostearic acid (Type 5681 of Unilever-Emery) was heated at a vacuum of 350 Torr, with stirring, in the presence of 3 g of butyl titanate, and in an atmosphere of nitrogen, so as to raise the temperature from 180° to 240° C within 3 hours, and the reaction water was simultaneously removed. The esterification was continued until an acid number of less than 2 was achieved. The glycerine partial ester was then deodorized for 2 hours at 170° C and filtered.

Acid Number = 1.0 Saponification No. = 161
Hydroxyl No. = 254 Density at 25° C = 0.948
Viscosity at 25° C = 451 cP
Turbidity point = 22° C

EXAMPLE 20

1000 g of the glycerine partial ester prepared in Example 19 was further esterified with 60 g of succinic acid anhydride in a 2-liter three-necked flask equipped with stirrer, thermometer, gas feed tube and water separator, under a nitrogen atmosphere and then under a vacuum of 20 Torr, so as to raise the temperature at approximately 10° C per hour from 140° to 220° C within 8 hours, down to an acid number of less than 1.

Acid number = 0.5 Saponification No. = 219
Hydroxyl No. = 181 Density at 25° C = 0.965
Viscosity at 25° C = 659 cP
Turbidity Point = 11° C

EXAMPLE 21

In a manner similar to Example 20, 1000 g of glycerine partial ester prepared in Example 1 was esterified with 100 g of succinic acid anhydride down to an acid number under 1.

Acid number = 0.8 Saponification No. = 254
Hydroxyl No. = 125 Density at 25° C = 0.976
Viscosity at 25° C = 1084 cP
Turbidity Point = 7° C

EXAMPLE 22

In a manner similar to Example 20, 1000 g of glycerine partial ester was esterified with 120 g of succinic acid anhydride to an acid number of less than 1.

Acid No. = 0.9 Saponification No. = 281
Hydroxyl No. = 110 Density at 25° C = 0.982
Viscosity at 25° C = 1603 cP
Turbidity Point = 5° C

EXAMPLE 23

In a manner similar to Example 20, 1000 g of glycerine partial ester was esterified with succinic acid anhydride to an acid number of less than 2.

Acid No. = 1.2 Saponification No. 315 Hydroxyl No. = 51

Density at 25° C = 0.996 Viscosity at 25° C = 3014 cP

Turbidity Point = below 0° C

EXAMPLE 24

In a manner similar to Example 20, 1000 g of glycerine partial ester was saponified with 260 g of succinic acid anhydride to an acid number under 2.

Acid No. = 1.8 Saponification No. = 354 Hydroxyl No. = 21

Density at 25° C = 1.016 Viscosity at 25° C = 42,050 cP

Turbidity Point = below 0° C

EXAMPLE 25

In a manner similar to Example 20, 1000 g of glycerine partial ester was esterified with 100 g of malonic acid down to an acid number less than 1.

Acid No. = 0.5 Saponification No. = 192 Hydroxyl No. = 232

Density at 25° C = 0.968 Viscosity at 25° C = 363 cP

Turbidity Point = 16° C

EXAMPLE 26

(Glycerine Partial Ester)

In a 4-liter three-necked flask a mixture of 2840 g (10 moles) of isostearic acid, 460 g (5 moles) of glycerine, 0.5 g of butyl titanate as catalyst, and 4 g of active charcoal was heated at a vacuum of 350 Torr from 180° C to 240° C within 2 hours, with vigorous stirring, in a nitrogen atmosphere. The reaction water that formed was simultaneously removed, and the glycerine partial ester was deodorized for 1 hour at 170° C, bleached, and filtered.

Acid No. = 9.0 Saponification No. = 183 Hydroxyl No. = 107

Density at 25° C = 0.957 Viscosity at 25° C = 281 cP

Turbidity Point = 12° C

EXAMPLE 27

1000 g of the glycerine partial ester prepared in Example 26 is further esterified with 50 g of maleic acid anhydride in the 2-liter three-necked flask under a nitrogen atmosphere and then under a vacuum of 20 Torr at a temperature increasing from 140° to 220° C at a rate of about 10° C per hour, until an acid number less than 2 is attained.

Acid No. = 1.7 Saponification No. = 209 Hydroxyl No. = 42

Density at 25° C = 0.960 Viscosity at 25° C = 305 cP

Turbidity Point = 2° C

EXAMPLE 28

In a manner analogous to Example 27, 1000 g of glycerine partial ester, prepared as in Example 26, was esterified with 50 g of fumaric acid down to an acid number under 2.

Acid No. = 1.3 Sapnification No. = 227 Hydroxyl No. = 48

Density at 25° C = 0.963 Viscosity at 25° C = 318 cP

Turbidity Point = 0° C

EXAMPLE 29

A mixture of 1136 g (4 moles) of isostearic acid, 368 g (4 moles) of glycerine, 228 g of glutaric acid, 0.2 g of butyl titanate and 2 g of active charcoal is heated with vigorous stirring under a nitrogen atmosphere from 140° to 200° C within 6 hours, and the reaction water is removed by applying a vacuum that is increased slowly from 760 to 20 Torr. Esterification continues until an acid number under 1 is achieved.

The ester mixture that is formed is deodorized for one hour at 160° C, bleached with 1% bleaching earth, and filtered in the pressure filter.

Acid No. = 0.7 Saponification No. = 265 Hydroxyl No. = 137

Density at 25° C = 0.982 Viscosity at 25° C = 968 cP

Turbidity Point = 7° C

EXAMPLE 30

In a manner analogous to Example 29, an ester mixture is prepared by using 143 g of 2-methylglutaric acid instead of glutaric acid, with an acid number under 1.

Acid No. = 0.9 Saponification No. = 224 Hydroxyl No. = 176

Density at 25° C = 0.975 Viscosity at 25° C = 524 cP

Turbidity Point = 15° C

EXAMPLE 31

In a manner similar to Example 29, an ester mixture is prepared with an acid number of less than 1, using 143 grams of 2-ethylsuccinic acid.

Acid No. = 0.5 Saponification No. = 225 Hydroxyl No. = 174

Density at 25° C = 0.978 Viscosity at 25° C = 572 cP

Turbidity Point = 7° C

EXAMPLE 32

In a manner similar to Example 29, an ester mixture is prepared with an acid number of less than 1, using 143 grams of adipic acid.

Acid No. = 0.3 Saponification No. = 229 Hydroxyl No. = 174

Density at 25° C = 0.980 Viscosity at 25° C = 614 cP

Turbidity Point = 8° C

EXAMPLE 33

In a manner similar to Example 29, an ester mixture is prepared with an acid number of less than 1, using 143 grams of sebacic acid.

Acid No. = 0.9 Saponification No. = 208 Hydroxyl No. = 200

Density at 25° C = 0.968 Viscosity at 25° C = 441 cP

Turbidity point = 20° C

EXAMPLE 34

With vigorous stirring in a nitrogen atmosphere, 184 g (2 moles) of glycerine, 77 g of trimethyl adipic acid, 0.1 g of butyl titanate, 2 g of active charcoal, and an ester mixture of 620 g (2 moles) of a branched $C_{18}$ and $C_{22}$ iso acid obtained by the thermal treatment of rape oil containing erucic acid by a method analogous to the preparation of isostearic acid, were heated within 8 hours from 140° to 240° C, and the reaction water that formed was removed by a slow increase in vacuum (760 to 20 Torr). The product, with an acid number under 2, was deodorized for 1 hour at 160° C, bleached, and pressure filtered.

Acid No. = 1.1 Saponification No. = 153 Hydroxyl No. = 218
Density at 25° C = 0.965 Viscosity at 25° C = 340 cP
Turbidity Point = 15° C

EXAMPLE 35

(Emulsion Tests)

The procedure of Example 16 was followed.

The preparation of the emulsion was performed at 80° C initially; the cooling to 30° C was performed over a period of 60 minutes.

Table 4

Emulsion Type A:
Oil base: petroleum jelly (Pharmaline V-15-DAB 7)
Composition of the Emulsions:

| Oil base 4: | 27 wt.-parts petroleum jelly |
| | 3 wt.-parts emulsifiers of Examples 1-16 (excepting Example 6) |
| Aqueous phase: | 0.3 wt.-parts MgSO$_4$ |
| | 3.0 wt.-parts glycerine |
| | 0.2 wt.-parts p-hydroxybenzoic acid propyl ester |
| | 66.5 wt.-parts water |

| Example No. | 6 mos. 25° C | 3 mos. 40° C | 2 wks. 55° C | Thaw-Freeze cycles −15° C (16h)/ +20° C (8h) |
|---|---|---|---|---|
| Pentaerythrigol monooleate | O(+) | I(−) | II(−) | 4x* |
| Sorbitan sesquioleate | O(+) | I(+) | II(+) | 8x* |
| 19 | | I(+) | II(+) | 6x* |
| 26 | O(+) | I(+) | II(+) | 5x* |
| 20 | O(+) | | | |
| 21 | all | all | all | all |
| 22 | O(+) | O(+) | O(+) | 12x |
| 25 | | | | |
| 23 and 27-34 | all O(+) | all O(+) | O(+) a few I(+) | 10x a few 8x |

*For purposes of comparison

EXAMPLE 36

Preparation of a gel-like adsorption base and the use of same as a basis for creams.

The emulsifiers prepared in Examples 19 to 34 (except Example 34) were compared as to their emulsion stabilizing action on the basis of an adsorption base as a practical example of their application.

COMPOSITION OF THE EMULSION 35 wt.-parts adsorption base (oil base 5)
65 wt.-parts aqueous phase
(62.5 wt.-parts water,
0.3 wt.-parts MgSO$_4$
0.3 wt.-parts p-hydroxybenzoic acid propyl ester
2.0 wt.-parts sorbitol)

COMPOSITION AND PREPARATION OF THE ADSORPTION BASE

Oil base 5

50 wt.-parts paraffin oil
25 wt.-parts MIGLYOL 812 ® (Mfr., Dynamit Nobel)
5 wt.-parts BENTONE 27 ® (Titangesellschaft, Leverkusen)
5 wt.-parts propylene glycol
15 wt.-parts of the emulsifiers of Examples 19 to 34 (except Example 24)

The components of the adsorption base are vigorously stirred together for 1 hour at 120° C. After cooling down to 80° C, 35 wt.-parts of the adsorption base are combined with 65 wt.-parts of the aqueous phase whose temperature is also 80° C, with constant stirring. Stirring is continued until the mass has cooled, and a smooth cream is obtained.

Table 5 shows the results of the stability tests.

Table 5

Emulsion Type B:
Oil base: paraffin oil and triglyceride

| Example No. | 6 mos. 25° C | 3 mos. 40° C | 2 wks. 55° C | Thaw-freeze cycles −15° C (16h)/ +20° C (8h) |
|---|---|---|---|---|
| Pentaerythritol monooleate | O(+) | I(−) | III(−) | 4x* |
| Sorbitan sesquioleate | O(+) | I(+) | II(+) | 8x* |
| 19 | O(+) | O(+) | II(−) | 6x* |
| 26 | O(+) | O(+) | II(+) | 6x* |
| 20 | O(+) | O(+) | O(+) | 10x |
| 21 | O(+) | O(+) | O(+) | 12x |
| 22 | O(+) | O(+) | O(+) | 12x |
| 25 | O(+) | O(+) | O(+) | 10x |
| 23 and 27–34 | all O(+) | all O(+) | I(+) a few O(+) | 8x a few 10x |

*for purposes of comparison.

EXAMPLE 37

The ester mixture prepared in Example 24 and having a low hydroxyl number and a high viscosity can be used in combination with any other ester mixture of a high hydroxyl number for the preparation of a stable water-in-oil emulsion, as for example:

OIL BASE 6

15 wt.-parts emulsifier (Example 24; hydroxyl No. 21)
20 wt.-parts ester mixture (Example 21; hydroxyl No. 125)
20 wt.-parts paraffin oil
30 wt.-parts petroleum jelly
15 wt.-parts isopropyl myristate

COMPOSITION OF THE EMULSION 30 wt.-parts oil base 6
70 wt.-parts aqueous phase
(0.3 wt.-parts MgSO$_4$
0.2 wt.-parts p-hydroxybenzoic acid propyl ester
3.0 wt.-parts 70% sorbitol solution
66.5 wt.-parts water)

EXAMPLE 38

The emulsifier prepared in Example 21 was tested for its emulsion stabilizing action in a water-in-oil lotion as an example of its application.

COMPOSITION OF THE EMULSION 33 wt.-parts oil base 7
67 wt.-parts aqueous phase
(0.3 wt.-parts MgSO$_4$
0.2 wt.-parts p-hydroxybenzoic acid propyl ester
3.0 wt.-parts 70% sorbitol solution
63.5 wt.-parts water)

COMPOSITION AND PREPARATION OF OIL BASE 7

50 wt.-parts paraffin oil
25 wt.-parts MIGLYOL ® 812 (mfr., Dynamit Nobel)

20 wt.-parts of the emulsifier of Example 3

2 wt.-parts Bentone ® 27 (Titangesellschaft, Leverkusen)

3 wt.-parts propylene glycol

The components of oil base 7 are vigorously stirred for one hour at 120° C. After the mixture has cooled down to 80° C, 33 wt.-parts of this oil base together with 67 wt.-parts of aqueous phase also at 80° C are cooled with constant stirring down to 30° C over at least 1 hour's time. The water-in-oil lotion thus prepared shows no oil separation whatever and no phase inversion after 2 weeks of storage.

EXAMPLE 39

In a one-liter flask equipped with stirrer, water separator, thermometer and gas feed tube, a mixture of 201 g (1.5 moles) of trimethylolpropane, 426 g (1.5 moles) of isostearic acid, 60 g of succinic acid anhydride, and 0.1 g of butyl titanate is heated with vigorous stirring in a nitrogen atmosphere from 140° to 200° C over a period of 6 hours, and the water of reaction is removed by a vacuum of 20 Torr. Esterification is continued until an acid number of less than 1 is reached. The ester mixture thus obtained is deodorized for one hour at 160° C, bleached with 1% bleaching earth, and filtered in a pressure filter.

Acid No. 1.0 Saponification No. 232 Hydroxyl number 157

Viscosity at 25° C = 1725 cP

EXAMPLE 40

In a manner similar to Example 39, a mixture of 201 g (1.5 moles) of trimethylolpropane, 426 g (1.5 moles) of isostearic acid, 109 g of adipic acid and 0.1 g of butyl titanate is heated with vigorous stirring under a nitrogen atmosphere from 140° to 220° C over a period of 6 hours, and the reaction water is removed by vacuum of 20 Torr. The product is deodorized, bleached and filtered as described above.

Acid No. = 2.0 Saponification No. = 252

Hydroxyl No. = 127 Viscosity at 25° C = 1350 cP

EXAMPLE 41

(Trimethylol propane partial ester)

In a 5-liter three-necked flask, a mixture of 2840 g (10 moles) of isostearic acid, 1340 g (10 moles) of trimethylolpropane in the presence of 0.5 g of butyl titanate as catalyst, and 4 g of active charcoal, is heated with vigorous stirring in a nitrogen atmosphere from 180° to 240° C over a period of 4 hours, under a vacuum of 20 Torr. The water of reaction is simultaneously removed, and the trimethylol propane ester is deodorized for 1 hour at 160° C, bleached and filtered.

Acid No. = 0.5 Saponification No. = 144 Hydroxyl No. = 272

EXAMPLE 42

1000 g of the trimethylol propane partial ester prepared in Example 41 is further esterified with 50 g of succinic acid anhydride in the two-liter three-necked flask provided with stirrer, thermometer, gas feed tube and water separator, at first under a nitrogen atmosphere and then in a vacuum of 20 Torr, by raising the temperature from 140° to 220° C over a period of 8 hours (temperature increase rate approximately 10° C/h), until an acid number under 1 is achieved.

Acid No. = 0.4 Saponification No. = 198 Hydroxyl No. = 185

Viscosity at 25° C = 871 cP

EXAMPLE 43

In a manner similar to Example 42, 1000 g of trimethylol propane partial ester, prepared as in Example 3, is further esterified with 100 g of adipic acid down to an acid number of less than 1.

Acid No. = 0.8 Saponification No. = 212 Hydroxyl No. = 178

Viscosity at 25° C = 850 cP

EXAMPLE 44

(Pentaerythritol partial ester)

In a 5-liter three-necked flask provided with stirrer, water separator, thermometer and gas feed tube, a mixture of 680 g (5 moles) of pentaerythritol, 2840 g (10 moles) of isostearic acid (Type 5681 of Unilever-Emmery) is esterified in the presence of 2 g of butyl titanate by heating it from 180° to 240° C over a period of 4 hours, with stirring and the simultaneous passage of nitrogen through the flask, at 20 Torr, and the reaction water that forms is simultaneously removed.

The esterification is performed until an acid number under 2 is achieved.

Acid No. = 1.4 Saponification No. = 151 Hydroxyl No. = 182

EXAMPLE 45

1000 g of the pentaerythritol partial ester prepared in Example 45 is further esterified with 80 g of succinic acid anhydride in the 2-liter three-necked flask, with vigorous stirring, in a nitrogen atmosphere, and then in a vacuum of 20 Torr, from 140° to 240° C for 8 hours (temperature increase approximately 10° C per hour), to an acid number under 1. The partial ester is then deodorized for 1 hour at 160° C and filtered.

Acid No. = 0.5 Saponification No. = 241 Hydroxyl No. = 78

Viscosity at 25° C = 3550 cP

EXAMPLE 46

In a manner similar to Example 45, 1000 g of pentaerythritol partial ester, prepared as in Example 4, was esterified with 100 g of adipic acid to an acid number under 1.

Acid No. = 0.8 Saponification No. = 251 Hydroxyl No. = 78

Viscosity at 25° C = 3100 cP.

EXAMPLE 47

In a manner similar to Example 45, 1000 g of pentaerythritol partial ester, prepared as in Example 45, was esterified with 100 g of succinic acid anhydride to an acid number under 2.

Acid No. = 1.3 Saponification No. = 260 Hydroxyl No. = 53

Viscosity at 25° C = 5050 cP.

EXAMPLE 48

(Emulsion tests)

The preparation of the emulsion was performed as in Example 35; the storage and evaluation were as described in Example 16.

Table 6

Emulsion Type A:
Oil base: Petroleum jelly (Pharmaline V-15-DAB 7)
Composition of the emulsions:

| | |
|---|---|
| Oil base 1: | 27 wt.-parts petroleum jelly |
| | 3 wt.-parts emulsifiers |
| | of Examples 1, 2, |
| | 4, 5, 7, 8 and 9 |
| Aqueous phase: | 0.3 wt.-parts $MgSO_4$ |
| | 3.0 wt.-parts glycerine |
| | 0.2 wt.-parts p-hydroxyben- |
| | zoic acid |
| | propyl ester |
| | 66.5 wt.-parts water |

| Example No. | 6 mos. 25° C | 3 mos. 40° C | 2 wks. 55° C | Freeze-thaw cycles −15° C (16h)/ +20° C (8H) |
|---|---|---|---|---|
| Pentaerythritol monooleate* | O(+) | I(−) | II(−) | 4x |
| Sorbitan sesquioleate* | O(+) | I(+) | II(+) | 8x |
| 39 | O(+) | O(+) | O(+) | 12x |
| 40 | O(+) | I(+) | I(+) | 8x |
| 42 | O(+) | O(+) | O(+) | 12x |
| 43 | O(+) | O(+) | I(+) | 10x |
| 45 | O(+) | O(+) | O(+) | 12x |
| 46 | O(+) | O(+) | I(+) | 10x |
| 47 | O(+) | O(+) | I(+) | 10x |

*For purposes of comparison.

What is claimed is:

1. Surface active, liquid, hydroxyl-containing mixed ester, having a hydroxyl number from 20 to 260, saponification numbers from 150 to 350 and acid number under 5 which is a condensation product of
   (a) 1 mole of glycerine, trimethylolpropane or pentaerythritol or a mixture thereof,
   (b) 1 to 2 moles of a saturated, branched, aliphatic monocarboxylic acid of 16 to 26 C atoms or a mixture thereof, and
   (c) 0.1 to 0.9 moles, of an aliphatic straight-chain or branched dicarboxylic acid of 3° to 10° C atoms, or an anhydride thereof or a mixture therof.

2. Mixed ester of claim 1, wherein the amount of (c) is 0.1 to 0.7 moles.

3. Mixed ester of claim 1, wherein (a) is glycerine.

4. Mixed ester of claim 3, wherein the amount of (c) is 0.2 to 0.6 moles.

5. Mixed ester of claim 1, wherein (a) is trimethanol propane or pentaerythritol.

6. Mixed ester of claim 5, wherein the amount of (c) is 0.2 to 0.7 moles.

7. Process of preparing a surface active liquid, hydroxyl-containing mixed ester which comprises contacting:
   (a) 1 mole of glycerine, trimethylolpropane or pentaerythritol or a mixture thereof, and
   (b) 1 to 2 moles of a saturated, branched, aliphatic monocarboxylic acid of 16° to 26° C atoms, or a mixture thereof,
at 100° to 250° C at a pressure and for a time sufficient for formation of a hydroxyl-containing partial ester of (a) and (b) and thereafter contacting the partial ester with
   (c) 0.1 to 0.9 moles of aliphatic straight chain or branched dicarboxylic acid of 3 to 10 carbon atoms or an anhydride thereof, or a mixture thereof
at 100° to 240° C, at a pressure and for a time sufficient for condensation of the partial ester and until an acid number under 5 is reached, to form said mixed ester by said condensation.

8. Process of claim 7, wherein the partial ester is produced in vacuum, and said mixed ester is produced in vacuum and has an acid number under 1.

9. Process of claim 7, wherein the amount of dicarboxylic acid is 0.1 to 0.7 moles.

10. Process of claim 7, wherein the partial ester has an acid number under 50.

11. Process of claim 10, wherein the partial ester is prepared at 160°–250° C, and has an acid number of less than 1.

12. Process of claim 7, wherein in the condensation for production of the mixed ester, the temperature is increased by about 8° to 12° C per hour.

13. Process of claim 12, wherein said temperature increase is 9° to 11° C per hour.

14. Process of claim 7, wherein the mixed ester is decolorized and deodorized.

15. Process of claim 7, wherein (a) is glycerine, the partial ester is prepared at 160° to 250° C, and the mixed ester is prepared at 140° to 220° C.

16. Process of claim 15, wherein the partial ester and the mixed ester are prepared in vacuum, the amount of (c) is 0.2 to 0.6 moles, and the acid number of the mixed ester is under 1.

17. Process of claim 15, wherein the partial ester is prepared at 200° to 250° C and the partial ester has an acid number under 50.

18. Process of claim 17, wherein the partial ester has an acid number under 1.

19. Process of claim 15, wherein in the condensation for the production of the mixed ester, the temperature is increased by about 8° to 12° C per hour.

20. Process of claim 19, wherein said temperature is increased 9° to 11° C per hour.

21. Process of claim 15, wherein the mixed ester is decolorized and deodorized.

22. Process of claim 7, wherein (a) is trimethylol propane or pentaerythritol, the partial ester is prepared at 160° to 250° C, and the mixed ester is prepared at 140°–240° C.

23. Process of claim 22, wherein the partial ester and the mixed ester are prepared in vacuum, the amount of (c) is 0.2 to 0.7 moles, and the acid number of the mixed ester is under 1.

24. Process of claim 22, wherein the partial ester has an acid number under 50.

25. Process of claim 24, wherein the partial ester is prepared at 200° to 250° C, and has an acid number under 1.

26. Process of claim 22, wherein in the condensation for the production of the mixed ester, the temperature is increased by about 8° to 12° C per hour.

27. Process of claim 26, wherein said temperature is increased 9° to 11° C per hour.

28. Process of claim 22, wherein the mixed ester is decolorized and deodorized.

29. Process of claim 7, wherein:
   (a) is glycerol,
   (b) is isostearic acid,
   (c) is succinic acid anhydride.

30. Mixed ester of claim 1, wherein the dicarboxylic acid is saturated.

31. Process of claim 7, wherein the dicarboxylic acid is saturated.

32. Process of preparing a surface active liquid, hydroxylcontaining mixed ester which comprises contacting:

(a) 1 mole of glycerine, trimethylolpropane or pentaerythritol or a mixture thereof, and
(b) 1 to 2 moles of a saturated, branched, aliphatic monocarboxylic acid of 16 to 26° C atoms, or a mixture thereof, and
(c) 0.1 to 0.9 moles of aliphatic straight chain or branched dicarboxylic acid of 3 to 10 cations or an anhydride thereof, or a mixture thereof, at 100° to 240° C, at a pressure and for a time sufficient for condensation to form said mixed ester and until an acid number under 5 is reached.

33. Process of claim 32, wherein the amount of dicarboxylic acid is 0.1 to 0.7 moles.

34. Process of claim 32, wherein the mixed ester is decolorized and deodorized.

35. Process of claim 32, wherein the temperature is 140° to 240° C.

36. Process of claim 32, wherein the temperature is 140° to 220° C.

37. Process of claim 32, wherein the mixed ester produced has an acid number under 5.

38. Mixed ester according to claim 1, wherein:
(a) is glycerol
(b) is isostearic acid
(c) is succinic acid anhydride.

* * * * *